(12) United States Patent
Meyers et al.

(10) Patent No.: US 8,080,240 B2
(45) Date of Patent: Dec. 20, 2011

(54) PARVOVIRUS METHODS AND COMPOSITIONS FOR KILLING NEOPLASTIC CELLS

(75) Inventors: Craig M. Meyers, Hummelstown, PA (US); Samina Alam, Hershey, PA (US)

(73) Assignee: The Penn State Research Foundation, University Park, PA (US)

(*) Notice: Subject to any disclaimer, the term of this patent is extended or adjusted under 35 U.S.C. 154(b) by 652 days.

(21) Appl. No.: 11/577,782

(22) PCT Filed: Oct. 21, 2005

(86) PCT No.: PCT/US2005/037930
§ 371 (c)(1),
(2), (4) Date: Apr. 23, 2007

(87) PCT Pub. No.: WO2006/047301
PCT Pub. Date: May 4, 2006

(65) Prior Publication Data
US 2009/0117081 A1    May 7, 2009

Related U.S. Application Data

(60) Provisional application No. 60/620,928, filed on Oct. 21, 2004.

(51) Int. Cl.
*A61K 39/04*    (2006.01)
*C12N 15/37*    (2006.01)
(52) U.S. Cl. .................. 424/93.1; 424/233.1; 435/320.1
(58) Field of Classification Search ............... 435/320.1; 424/93.1
See application file for complete search history.

(56) References Cited

OTHER PUBLICATIONS

Eisold et al. Int. J. Cancer 2002, vol. 100, pp. 606-614.*
Coker et al. Experimental and Molecular Pathology, 2001, vol. 70, No. 2, pp. 83-89.*
Berns K. Microbiological Reviews 1990, pp. 316-329.*
Klein-Bauernschmitt et al. European Journal of Caner 1996, vol. 32A, No. 10, pp. 1774-1780.*
Fan, P-D., "Replication or rep-cap Gene is Essential for the High-Effeciency Production of Recombinant AAV.", Human Gene Therapy, 8:87-98 (1997).
Moehler, M., et al., "Effective infection, apoptotic cell killing and gene transfer of human hepatoma cells but not primary hepatocytes by arvovirus H1 and derived vectors", Cancer Gene Therapy, 8(3):158-167 (2001).
Olijslagers, A., et al., "Potentiation of a recombinant oncolytic parvovirus by expression of apoptin", Cancer Gene Therapy, 8(12):958-965 (2001).
Rohr, U-P., et al., "Non-small lung cancer cells are prime targets for p53 gene transfer medicated by a recombinant adeno-associated virus type-2 vector", Cancer Gene Therapy, 10:898-908 (2003).
Smith, E., et al., "Oncolytic viruses as novel anticancer agents: turning one scourge against another", Exp. Pin. Drugs, 9(2):311-327 (2000).
Wollmann, G. et al., "Targeting Human Glioblastoma Cells: Comparison of Nine Viruses with Oncolytic Potential", J. Virol. 79(10:6005-6022 (2005).

* cited by examiner

*Primary Examiner* — Bao Qun Li
(74) *Attorney, Agent, or Firm* — McKee, Voorhees & Sease, P.L.C.

(57) ABSTRACT

According to the invention, parvoviruses such as the adeno-associated virus Type 2 (AAV2) are found to be oncolytic, selectively mediating apoptosis in cancer cells and their precursors, while leaving healthy cells intact. The invention thus comprises a method of killing cancer and other neoplastic and preneoplastic cells by administration of AAV2 virus, viral particles, products or replication incompetent vectors derived there from to said cells, and pharmaceutical compositions comprising the same.

6 Claims, 7 Drawing Sheets

PARVOVIRUS METHODS AND COMPOSITIONS FOR KILLING NEOPLASTIC CELLS

CROSS-REFERENCE TO RELATED APPLICATIONS

This application is a conversion of and claims priority to U.S. Provisional Patent Application No. 60/620,928 filed Oct. 21, 2004, which is herein incorporated by reference in its entirety.

GRANT REFERENCE

Work for this invention was funded in part by a grant from the United States Government National Institutes of Health, NIH Grant Number CA79006. The Government may have certain rights in this invention.

BACKGROUND OF THE INVENTION

The limited ability of anti-neoplastic therapy to distinguish neoplastic from normal cells continues to be a primary hurdle in the treatment and irradiation of neoplastic, tumor or other cancerous cells. Distinguishing between the two on the basis of proliferative behavior has shown some success, but the search for biochemical characteristics of neoplastic cells that are tumor specific rather than proliferation specific remains the focus of further research. Unfortunately current molecular genetic studies have failed to support the expectation that such characteristics are a consistent feature of neoplastic cells. Rather these studies suggest that the neoplastic state can be explained without postulating tumor specific functions, but merely the operation of normal proliferation-specific functions at abnormal levels, as a result of changes (sometimes minimal) in the structure of growth-regulatory genes or changes in their number or chromosomal environment. This conclusion suggests that continued search for highly specific attributes of neoplastic cells cannot be relied upon for a general solution to the problems of cancer therapy.

As can be seen there is a continuing need in the art for cancer therapy that specifically and selectively targets and kills cancer cells and their precursors.

In general, gene therapy for cancers and many diseases offers novel treatment strategies and leads to the destruction of malignant and suboptimal cells. Ideally, the goal in all cases is to target deregulated cells while leaving the surrounding cells healthy and intact. Major cancer therapy approaches have included chemosensitization, cytokine gene transfer, inactivation of proto-oncogene expression, replacement of defective tumor suppressor genes, and transduction of oncolytic viruses. Included in this category are Adeno-associated virus-derived vectors which have been shown to be nonpathogenic vectors with potential for cancer gene therapy.

SUMMARY OF THE INVENTION

According to the invention, applicants have found that parvoviruses such as the adeno-associated virus Type 2 (AAV2) selectively mediate apoptosis in cancer cells and their precursors, while leaving healthy cells intact. The invention thus comprises a method of killing cancer and other neoplastic and preneoplastic cells by administration of AAV2 virus, viral particles, products or replication incompetent vectors derived there from to said cells. AAV2 is a non-pathogenic tumor suppressive virus which has been shown to perturb cell cycle regulation of infected cells. Applicant's have surprisingly found that administration of AAV2, its protein products or viral particles to cancer cells and/or their precursers results in cell death of cancer cells in approximately 6 days post infection while similar administration to noncancerous cells results in no such effects. Applicants have demonstrated in cervical cancer cells that this cell death is apototic in nature and occurs during all stages of carcinogenic progression including preneoplastic cervical intraepithelial neoplasia type 1 up to cervical invasive carcinoma cells. The invention also includes prophylactic treatment for cancer prevention for treating all stages of cancer including the earliest stages that may be undetectable by clinical observations. Normal, non-cancerous cells infected by AAV2 did not undergo apoptosis and displayed no cytopathic effects. Quite unexpectedly, applications have also found that AAV2 provides induction of apoptosis in cancers other than cervical including squamous cell carcinomas, breast carcinoma, prostate carcinoma and melanoma.

In a preferred embodiment the AAV2 viral particles are created in vivo with the presence of a helper virus including but not limited to HPV, adenovirus, herpesvirus, or vaccinia virus provides for enhancer/helper functions for replication of AAV and virus production in the cell. In a most preferred embodiment the method is used to kill cancer cells and their precursors which are known to be associated with the presence of one of the aforementioned helper viruses, such as cervical cancer cells which are associated with the presence of HPV virus.

Also included in the invention are pharmaceutical compositions for killing cancer cells which includes an AAV2 virus, an AAV2 virus particle or an AAV2 vector wherein the AAV2 virus itself is the therapeutic agent, further compositions include AAV2 gene products (rep proteins), genomic AAV2 sequences (such as ITR hair-pin ends), capsid proteins, or other treatment protocols which activate the same cell signaling pathways activated upon virus binding to cell surface receptors. While not wishing to be bound by any theory, it is postulated that the proteins produced by parvoviruses, (rep proteins), the nucleotide hairpin ends, or possibly the capsid proteins produced by the virus cause the desired effects. The invention also contemplates use of other elements which will activate the identical pathways as the parvovirus AAV2, according to the descriptions herein.

DETAILED DESCRIPTION OF THE INVENTION

Figure 1:
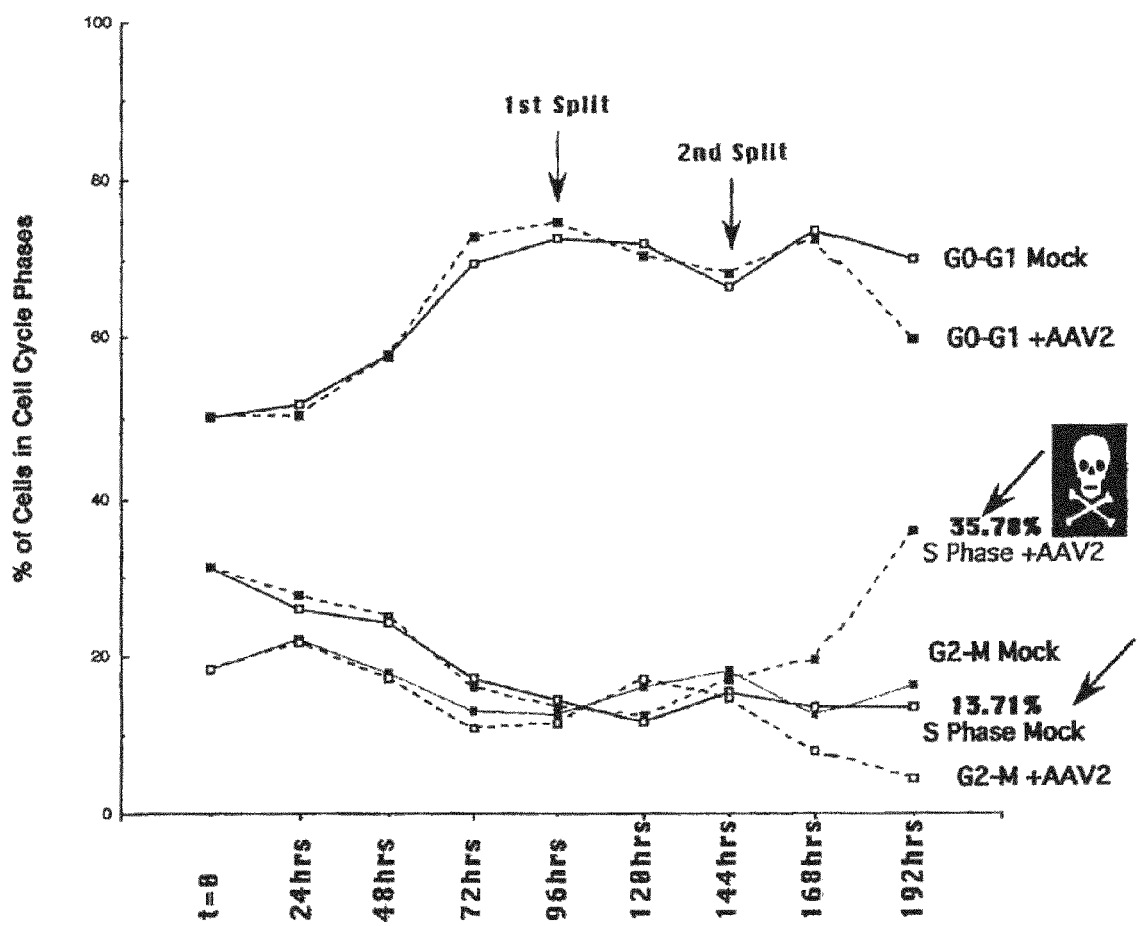
FIG. 1 is a graph showing the percentage of cells in cell cycle phase over time. FACS analysis of the mock and AAV2 infected cells suggested that massive cell death was accompanied by a more than 20% increase in the number of cells with S phase DNA content.

The present invention provides a method of treating a neoplasm in an animal by using an oncolytic virus, particularly a Parvovirus, such as AAV2. According to the invention Applicant's have determined that the virus AAV2 and/or its viral proteins are oncolytic to a variety of cancer cells. The cell killing was demonstrated both with and without the presence of helper virus.

Because the AAV2 virus is nonpathogenic, the virus or its proteins may be used in a prophylactic protocol to protect a patient from cancer. According the this embodiment a patient at risk for neoplasia may be treated by administration of the AAV2 virus or proteins as described herein.

Prior to describing the invention in further detail, the terms used in this application are defined as follows unless otherwise indicated.

DEFINITIONS

A "neoplastic cell", "tumor cell", or "cell with a proliferative disorder" refers to a cell which proliferates at an abnormally high rate. A new growth comprising neoplastic cells is a "neoplasm", also known as a "tumor". A tumor is an abnormal tissue growth, generally forming a distinct mass that grows by cellular proliferation more rapidly than normal tissue growth. A tumor may show partial or total lack of structural organization and functional coordination with normal tissue. As used herein, a tumor is intended to encompass hematopoietic tumors as well as solid tumors.

A tumor may be benign (benign tumor) or malignant (malignant tumor or cancer). Malignant tumors can be broadly classified into three major types. Malignant tumors arising from epithelial structures are called carcinomas; malignant tumors that originate from connective tissues such as muscle, cartilage, fat, or bone are called sarcomas; and malignant tumors affecting hematopoietic structures (structures pertaining to the formation of blood cells) including components of the immune system, are called leukemias and lymphomas. Other tumors include, but are not limited to neurofibromatosis.

A "mutation" may be a deletion, insertion, or substitution of any nucleotide(s) or amino acid(s).

"Infection by parvovirus" refers to the entry and replication of Parvovirus in a cell. Similarly, "infection of a tumor by parvovirus" refers to the entry and replication of parvovirus in the cells of the tumor.

"AAV2" refers to any virus whether naturally occurring, modified or recombinant which retains the oncolytic properties of the AAV2 viruses described herein.

"Helper virus" refers to any virus or viral particle that helps the AAV2 to replicate. Helper viruses include but are not limited to adenovirus, herpesvirus, vaccinia virus, or human papillomaviruses or their helper proteins.

The AAV2 virus may be naturally occurring or modified. The virus is "naturally occurring" when it can be isolated from a source in nature and has not been intentionally modified by humans in the laboratory. For example, the adeno associated virus can be from a "field source", that is, from a human who has been infected with the virus.

The AAV2 virus may be modified but still capable of lytically infecting a mammalian cell. The virus may be chemically or biochemically pretreated (e.g., by treatment with a protease, such as chymotrypsin or trypsin) prior to administration to the proliferating cells. Pretreatment with a protease removes the outer coat or capsid of the virus and may increase the infectivity of the virus. The virus may be coated in a liposome or micelle. For example, the virion may be treated with chymotrypsin in the presence of micelle forming concentrations of alkyl sulfate detergents to generate a new infectious subvirion particle.

The AAV2 virus may be a recombinant (i.e., reasserted) virus resulting from the recombination/reassortment of genomic segments from two or more genetically distinct adeno associated viruses. Recombination/reassortment of virus genomic segments may occur in nature following infection of a host organism with at least two genetically distinct viruses. Recombinant virions can also be generated in cell culture, for example, by co-infection of permissive host cells with genetically distinct viruses.

Accordingly, the invention contemplates the use of a recombinant AAV2 virus resulting from reassortment of genome segments from two or more genetically distinct AAV2 viruses. The invention further contemplates the use of recombinant viruses resulting from reassortment of genome. segments from two or more genetically distinct viruses wherein at least one parental virus is genetically engineered, comprises one or more chemically synthesized genomic segment, has been treated with chemical or physical mutagens, or is itself the result of a recombination event. The invention further contemplates the use of the recombinant AAV 2 virus that has undergone recombination in the presence of chemical mutagens, including but not limited to dimethyl sulfate and ethidium bromide, or physical mutagens, including but not limited to ultraviolet light and other forms of radiation.

The invention further contemplates the use of recombinant AAV2 viruses that comprise deletions or duplications in one or more genome segments, that comprise additional genetic information as a result of recombination with a host cell genome, or that comprise synthetic genes.

The AAV2 virus may be modified by incorporation of mutated coat proteins, such as for example, into the virion outer capsid. The proteins may be mutated by replacement, insertion, or deletion. Replacement includes the insertion of different amino acids in place of the native amino acids. Insertions include the insertion of additional amino acid residues into the protein at one or more locations. Deletions include deletions of one or more amino acid residues in the protein. Such mutations may be generated by methods known in the art. For example, oligonucleotide site directed mutagenesis of the gene encoding for one of the coat proteins could result in the generation of the desired mutant coat protein. Expression of the mutated protein in AAV2 virus infected mammalian cells in vitro such as COS 1 cells will result in the incorporation of the mutated protein into the AAV2 virus virion particle (Turner and Duncan, 1992; Duncan et al., 1991; Mah et al., 1990).

While little or no host reaction was observed, the AAV2 virus may also be modified to even further reduce or eliminate an immune reaction to the virus. Such a modified virus is termed "immunoprotected AAV2 virus". Such modifications could include packaging of the virus in a liposome, a micelle, or other vehicle to mask the virus from the immune system. Alternatively, the outer capsid of the virus virion particle may be removed since the proteins present in the outer capsid are the major determinant of the host humoral and cellular responses.

An "immunoprotected virus" is a virus modified to reduce or eliminate an immune reaction to the virus. The modifications could include packaging of the virus in a liposome, a micelle, or other vehicle to mask the virus from the host immune system. Alternatively, the outer capsid of the virus virion particle may be removed since the proteins present in the outer capsid are the major determinant of the host humoral and cellular responses. In addition to reducing or eliminating immune responses, the modifications may also reduce non-specific uptake of the virus in normal tissues.

An "oncolytic virus" is a virus that preferentially replicates in, and kills, neoplastic cells. An oncolytic virus may be a naturally occurring virus or an engineered virus. Oncolytic viruses also encompass immunoprotected and reassortant viruses as described in detail for virus.

"Administration" of a virus to a subject refers to the act of administering the virus to a subject in a manner so that it contacts the target neoplastic and pre-neoplastic cells. The route by which the virus is administered, as well as the formulation, carrier or vehicle, will depend on the location as well as the type of the target cells.

The term "substantial lysis" means at least about 10% of the cells of a neoplasm are lysed. More preferably, at least about 20%, 30%, 40%, 50%, 60%, 70%, 80% or 90% of the cells are lysed. Most preferably, at least about 95% of the cells are lysed. The percentage of lysis can be determined, for example, by measuring the reduction in the size of the tumor or reduction of symptoms of the tumor.

A "mammal suspected of having a neoplasm" is a mammal that has a genetic disposition for a tumor, or a mammal in which the tumor or substantially all of the tumor has been surgically removed but is suspected of harboring residual tumor cells.

"Treating or alleviating a tumor" means alleviating or eliminating the symptoms of a tumor, or slowing down the progress of the tumor. The alleviation is preferably at least about 10%, more preferably at least about 20%, 30%, 40%, 50%, 60%, 70%, 80%, 90% or 95%.

A "metastatic tumor" is a tumor that has metastasized from a tumor located at another place in the same animal.

An "effective amount" is an amount of an agent that is sufficient to result in the intended effect. For an oncolytic virus used to treat or ameliorate a tumor, an effective amount is an amount of the virus sufficient to alleviate or eliminate the symptoms of the tumor or to slow down the progress of the tumor.

The terms "immunosuppressant" or "immune suppressive agent" include conventional immunosuppressants, immuno inhibitors, antibodies, and conditions such as radiation therapy or 11V infection which result in compromise of the immune system.

In addition to AAV2, other oncolytic viruses can be used in combination with AAV2 to practice the present invention in the same manner as AAV2. These viruses may be naturally existing, or they may be modified or mutated.

A few such oncolytic viruses are discussed below, and a person of ordinary skill in the art can practice the present invention using additional oncolytic viruses as well according to the disclosure herein and knowledge available in the art. The oncolytic virus may be a member in the family of myoviridae, siphoviridae, podoviridae, teciviridae, corticoviridae, plasmaviridae, lipothrixviridae, fuselloviridae, poxyiridac, iridoviridae, phycodnaviridae, baculoviridae, herpesviridae, adenoviridae, Papillomaviridae, polyomaviridae, polydnaviridae, inoviridae, microviridae, geminiviridac, circoviridae, hepadnaviridae, retroviridae, cyctoviridae, reoviridae, bimaviridae, paramyxoviridae, rhabdoviridae, filoviridae, orthomyxoviridae, bunyaviridae, arenaviridac, leviviridae, picornaviridae, sequiviridae, comoviridae, potyviridae, caliciviridae, astroviridae, nodaviridae, tetraviridae, tombusviridae, coronaviridae, glaviviridae, togaviridae, or barnaviridae. As with AAV2, immunoprotected or reassortant viruses of other oncolytic viruses are also encompassed in the present invention. Furthermore, a combination of at least two oncolytic viruses, including AAV2, can also be employed to practice the present invention.

The route by which the virus is administered, as well as the formulation, carrier or vehicle, will depend on the location as well as the type of the neoplasm. A wide variety of administration routes can be employed. For example, for a solid neoplasm that is accessible, the virus can be administered by injection directly to the neoplasm. For a hematopoietic neoplasm, for example, the virus can be administered intravenously or intravascularly. For neoplasms that are not easily accessible within the body, such as metastases or brain tumors, the virus is administered in a manner such that it can be transported systemically through the body of the mammal and thereby reach the neoplasm (e.g., intrathecally, intravenously, or intramuscularly). Alternatively, the virus can be administered directly to a single solid neoplasm, where it then is carried systemically through the body to metastases. The virus can also be administered subcutaneously, intraperitoneally, topically (e.g., for melanoma), orally (e.g., for oral or esophageal neoplasm), rectally (e.g., for colorectal neoplasm), vaginally (e.g., for cervical or vaginal neoplasm), nasally or by inhalation (e.g., for lung neoplasm).

The virus can be administered systemically to mammals which are immune compromised or which have not developed immunity to the virus. In such cases, viruses that are administered systemically, i.e., by intravenous injection, will spread to the locations of the neoplastic cells, resulting in lysis of the cells.

This invention also includes pharmaceutical compositions which contain, as the active ingredient, one or more of the AAV2 viruses, or its active proteins, hairpins, capsid proteins or any component which retains the oncolytic properties of the AAV2 virus as described herein, associated with pharmaceutically acceptable carriers or excipients. The invention further includes pharmaceutical compositions which contain, as the active ingredient, one or more of the viruses, along with an appropriate immunosuppressant, associated with pharmaceutically acceptable carriers or excipients. In making the compositions of this invention, the active ingredient/virus is usually mixed with an excipient, diluted by an excipient, or enclosed within such a carrier which can be in the form of a capsule, sachet, paper or other container. When the pharmaceutically acceptable excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propyl hydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredient/virus is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills, and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device, or the nebulizing device may be attached to a face mask tent or intermittent positive pressure breathing machine. Solution, suspension, or powder compositions may be administered, preferably orally or nasally, from devices which deliver the formulation in an appropriate manner.

Another preferred formulation employed in the methods of the present invention employs transdermal delivery devices ("patches"). Such transdermal patches may be used to provide continuous or discontinuous infusion of the virus of the present invention in controlled amounts. The construction and use of transdermal patches for the delivery of pharmaceutical agents is well known in the art. See, e.g., U.S. Pat. No. 5,023,252, herein incorporated by reference. Such patches may be constructed for continuous, pulsatile, or on-demand delivery of pharmaceutical agents.

Other suitable formulations for use in the present invention can be found in Remington's Pharmaceutical Sciences.

The AAV2 virus or the pharmaceutical composition comprising the virus may be packaged into convenient kits providing the necessary materials packaged into suitable containers. It is contemplated that the kits may also include chemotherapeutic agents and/or anti-antivirus antibody.

The AAV2 is administered in an amount that is sufficient to treat the neoplasm (e.g., an "effective amount"). A neoplasm is "treated" when administration of virus to the proliferating cells effects lysis of the proliferating cells. This may result in a reduction in size of the neoplasm or a complete elimination of the neoplasm. The reduction in size of the neoplasm, or elimination of the neoplasm, is generally caused by lysis of neoplastic cells ("oncolysis") by the virus. Preferably the effective amount is that amount able to inhibit tumor cell growth. Preferably the effective amount is from about 1.0 pfu/kg body weight to about $10^{15}$ pfu/kg body weight, and more preferably from about $10^2$ pfu/kg body weight to about $10^{13}$ pfu/kg body weight. For example, for treatment of a human, approximately $10^2$ to $10^{17}$ pfU of equivalent number of infectious particles or equivalent MOI of virus can be used, depending on the type, size, and number of tumors present. The effective amount will be determined on an individual basis and may be based, at least in part, on consideration of the type of virus; the chosen route of administration; the individual's size, age, gender; the severity of the patient's symptoms; the size and other characteristics of the neoplasm; and the like. The course of therapy may last from several days to several months or until diminution of the disease is achieved.

The virus can be administered in a single dose, or multiple doses (i.e., more than one dose). The multiple doses can be administered concurrently, or consecutively (e.g., over a period of days or weeks). The virus can also be administered to more than one neoplasm in the same individual.

The compositions are preferably formulated in a unit dosage form, each dosage containing from about $10^2$ pfus to about $10^{13}$ pfu of the virus. The term "unit dosage forms" refers to physically discrete units suitable as unitary dosages for human subjects and other mammals, each unit containing a predetermined quantity of virus calculated to produce the desired therapeutic effect, in association with a suitable pharmaceutical excipient.

It has been found that the virus is effective for the treatment of solid neoplasms in immunocompetent mammals. Administration of unmodified virus directly to the neoplasm results in oncolysis of the neoplastic cells and reduction in the size of the tumor.

It is contemplated that the virus may be administered in conjunction with surgery or removal of the neoplasm. Therefore, provided herewith are methods for the treatment of a solid neoplasm comprising surgical removal of the neoplasm and administration of a virus at or near to the site of the neoplasm.

It is contemplated that the virus may be administered in conjunction with or in addition to radiation therapy.

It is further contemplated that the virus of the present invention may be administered in conjunction with or in addition to one or more known anticancer compounds or chemotherapeutic agents. Chemotherapeutic agents are compounds which may inhibit the growth of tumors. Such agents, include, but are not limited to, 5-fluorouracil, mitomycin C, methotrexate, hydroxyurea, cyclophosphamide, dacarbazine, mitoxantrone, anthracyclins (Epirubicin and Doxurubicin), antibodies to receptors, such as herceptin, etoposide, pregnasome, platinum compounds such as carboplatin and cisplatin, taxanes such as taxol and taxotere, hormone therapies such as tamoxifen and anti-estrogens, interferons, aromatase inhibitors, progestational agents and LHRH analogs.

The viruses of the present invention have been found to reduce the growth of tumors that are metastatic. In an embodiment of the invention, a method is provided for reducing the growth of metastastic tumors in a mammal comprising administering an effective amount of a virus to the mammal.

In order to further illustrate the present invention and advantages thereof, the following specific examples are given but are not meant to limit the scope of the claims in any way.

EXAMPLES

Oncosuppressive Property of AAV2 is Mediated by Targeting Viral DNA Replication AAV2 is ubiquitous, non-pathogenic, anogenital virus with tumor suppressive properties. Seroepidemiological data have clearly shown a negative association between AAV2 infection and the incidence of cervical cancer. In this respect, it is of interest to note that majority of the general population is seropositive for AAV2, whereas only a small fraction of patients with genital cancer were found to be seropositive for AAV2. Thus AAV2 exerts a protective effect against the development of cervical cancer. AAV2 is a helper-dependent, human Parvovirus, in that it requires the presence of helperviruses for its own replication. In turn, AAV inhibits the replication, transcription and virion morphogenesis of its helper virus. The mechanism of AAV2 mediated interference with its helper-virus life-cycle is related to its interference with helper-virus replication, promoter activates as well as oncogene expression. Thus far, the helper functions have been found to be provided by adenovirus, herpesvirus, or vaccinia virus. In addition, our laboratory has recently demonstrated that the human papillomaviruses are also capable of providing such helper functions.

A well characterized cell line in use in our laboratory is the CIN-612 9E cell line which maintains episomal copies of the Human Papillomavirus Type 31b (HPV31b). This cell line is a biopsy derived cell line from a patient with a low grade cervical lesion. Utilizing a HPV31b positive differentiation dependent organotypic raft culture system we have recently reported that HPV31b provides complete "enhancer/helper" functions for AAV2 replication and infectious virion morphogenesis. In turn, AAV2 inhibits the replication of HPV31b, thus decreasing the viral load and carcinogenic potential of the tissue.

AAV2 Can Also Mediate its Oncosuppressive Properties Via Modulation of the Cell Cycle In addition to interfering with helper virus DNA replication and promoter activity, AAV2 also mediates its oncosuppressive properties via perturbing cell cycle regulation. AAV2 infection has been shown to upregulate the expression of differentiation markers and markers of cellular senescence. AAV2 has the unique ability to mediate oncosuppressive effects via cell cycle modulation in naturally occurring tumor derived cell lines as well as cell lines which have been initiated with carcinogens. The ability of AAV2 to affect cell cycle regulation has been clearly demonstrated in a comprehensive study utilizing primary human fibroblasts derived from a tonsillectomy. In this study by Hermanns et. al, a thorough evaluation of the effect of AAV2 on cell cycle regulation in primary fibroblasts was presented. Infection was accompanied by Rb hypophosphorylation, suggesting a block in the G1 phase of the cell cycle. In addition, the expression of the universal CDK inhibitor p21/WAF1 was upregulated compared to mock samples. p21 is a unique CDK inhibitor in that it inhibits the activity of all cyclin-CDK complexes as well as being a potent tumor suppressor and regulator of cellular senescence. Although the results in the study by Hermanns et. al. clearly show cell cycle targeted effects of AAV2 in primary cells, one may argue that fibroblasts are not the normal host for AAV2. Rather, the anogenital localization of AAV2 places this virus in close proximity with the same tissue which could be infected by HPV suggesting that AAV2 also has tropism for keratinocytes.

We have previously demonstrated the negative effect of AAV2 on HPV replication in the differentiation dependent raft culture system. We wished to correlate this data with cell cycle changes which occur upon AAV2 superinfection of HPV infected cells. Under normal conditions HPV oncogenes E6 and E7 deregulate the expression and function of the tumor suppressors p53 and Rb respectively. Since AAV2 positively targets cells expressing viral oncogenes, we wished to determine the effect of cell cycle changes in an HPV positive cell line, which would enable us to correlate this data with the oncosuppression of HPV mediated by AAV2 via inhibition of HPV replication.

Results

Figure 2:
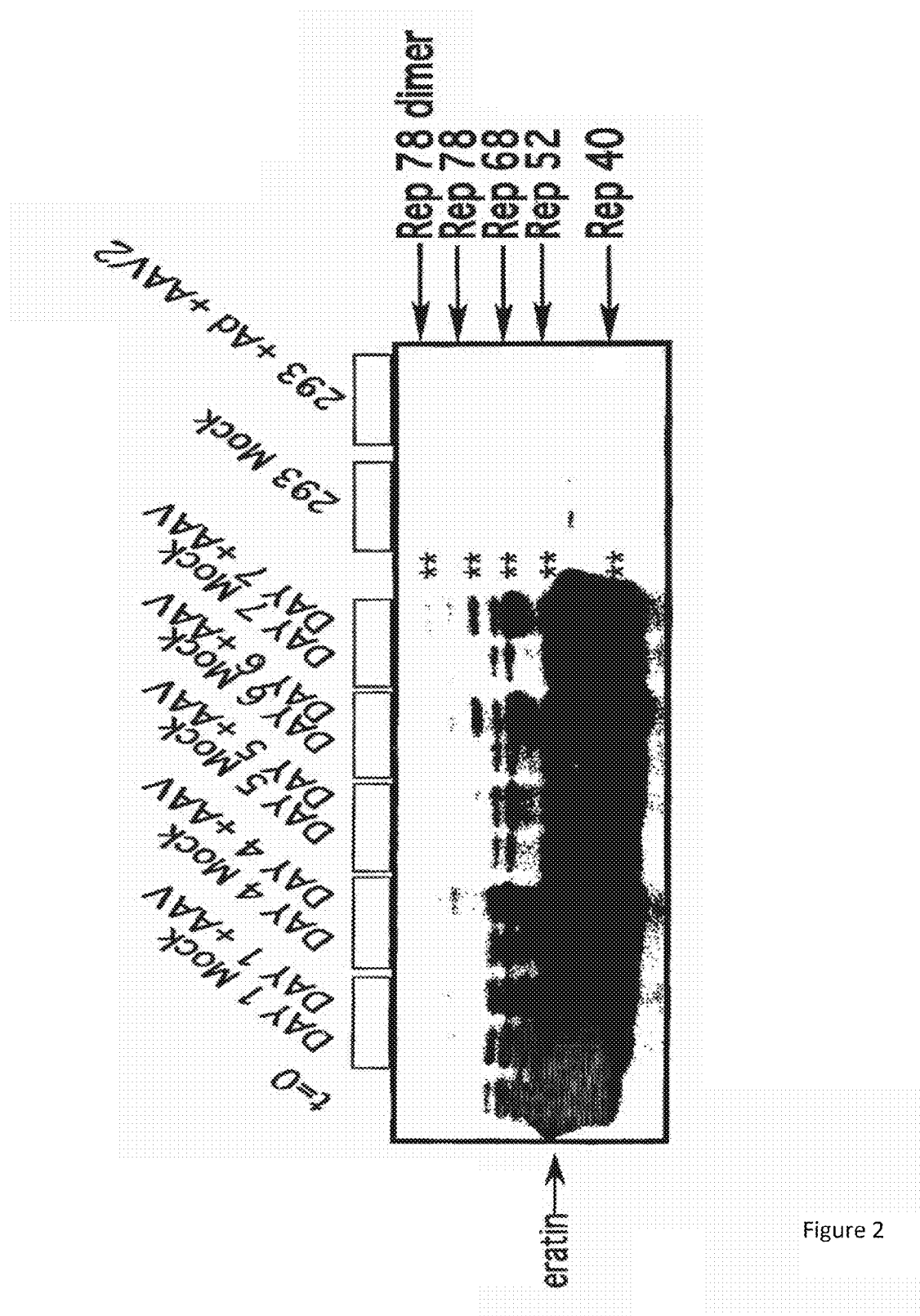
FIG. 2 shows the result of Western Blot analysis of cell extracts showing expression of the four AAV2 Rep proteins Rep78, Rep68, Rep52 and Rep40 late in the infection stage.
Figure 3:
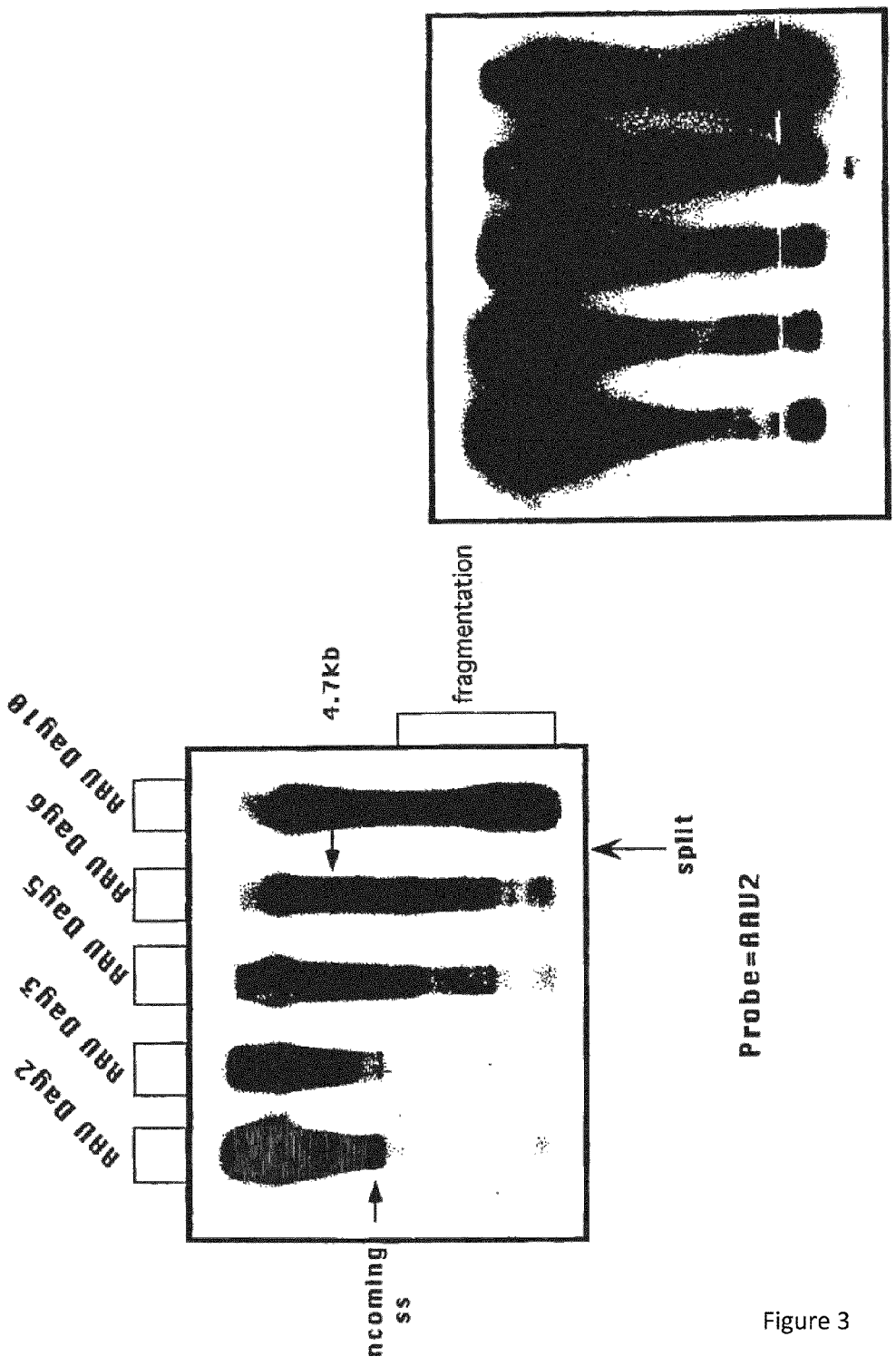
FIG. 3 shows the results of Southern Blot analysis, demonstrating that AAV2 replicated weakly in the AAV2 infected cells as evidenced by the lack of the 4.7 kb replicative monomer.
Figure 4:
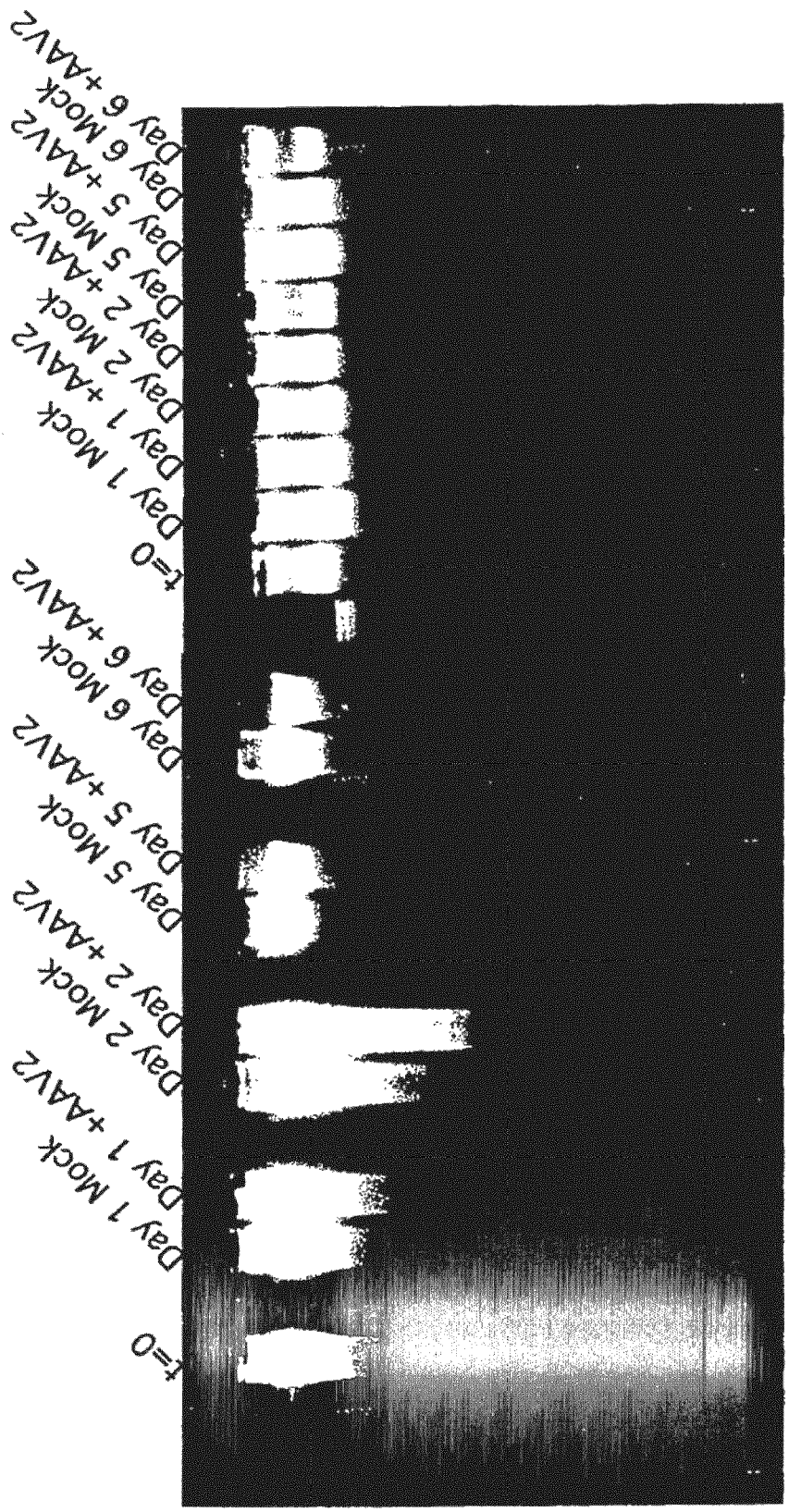
FIG. 4 shows Hirt DNA extraction from the mock infected and AAV2 infected cells and DNA fragmentation analysis. AAV2 infected CIN-612 9E cells underwent significant apoptosis as evidenced by DNA fragmentation analysis. But normal noncancerous cells were unaffected.

We infected subconfluent CIN-612 9E monolayer cell cultures with AAV2 and cultured them over a period of 7 days. The cells were split on Day 2 and Day 4, approximately at the times when the cells were 80% confluent. On Day 6 and Day 7 we visually observed extensive cell death among the AAV2 superinfected CIN-612 9E cells. At this stage, FACS analysis of the mock and AAV2 infected cells suggested that massive cell death was accompanied by a more than 20% increase in the number of cells with S phase DNA content (FIG. 1). We wanted to determine whether the AAV2 mediated cell death could be correlated with AAV2 encoded nonstructural Rep protein expression. Therefore, we performed Western blot analysis of cell extracts from the mock and AAV2 infected CIN-612 9E cells. We observed quantitative expression of the four AAV2 Rep proteins Rep78, Rep68, Rep52 and Rep40 late in the infection stage (FIG. 2). We performed Southern blot analysis to determine the status of AAV2 replication utilizing an AAV2 specific probe. AAV2 replicated weakly in the AAV2 infected cells as evidenced by the lack of the 4.7 kb replicative monomer (FIG. 3). This southern probe also bound to low molecular weight bands. The detection of these fragmented bands was suggestive of apoptosis. In order to determine whether AAV2 infection mediated an apoptotic response in the CIN-612 9E cell line, we performed Hirt DNA extraction from the mock infected and AAV2 infected cells and carried out a DNA fragmentation analysis (FIG. 4). AAV2 infected CIN-612 9E cells underwent significant apoptosis as evidenced by DNA fragmentation analysis, whereas we were unable to detect apoptosis in the mock infected controls. As an additional control, an identical experiment was performed utilizing primary human foreskin keratinocytes. We compared mock infected and AAV2 infected keratinocytes in a similar DNA fragmentation assay. Interestingly, primary human foreskin keratinocytes infected with AAV2 showed no such apoptotic response, suggesting that the AAV2 mediated apoptosis was specific to the HPV31b containing cell line.

Figure 5:
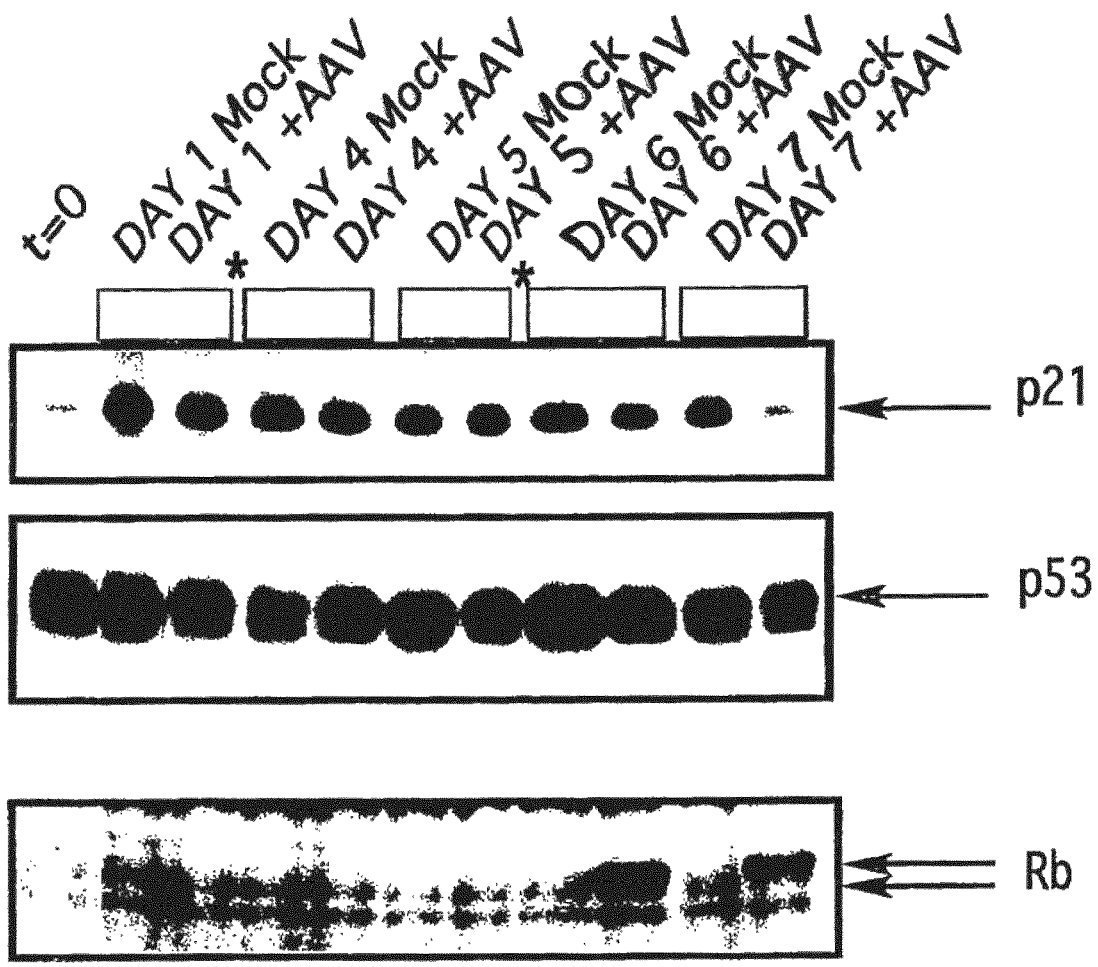
FIG. 5 is an agarose gel electrophoresis showing that AAV2 mediated apoptosis in the CIN-612 9E cells could be correlated with a consistent decrease in p21 levels as well as a decrease in tumor suppressor p53 levels.

AAV2 mediated apoptosis in the CI-612 9E cells could be correlated with a consistent decrease in p21 levels as well as a decrease in tumor suppressor p53 levels (FIG. 5). Interestingly, expression of the Rb tumor suppressor was significantly upregulated and stabilized, suggesting that AAV2 infection significantly modulates HPV31b E7 activity or expression of the E7 transcript from the HPV31b early promoter. In addition, Rb was predominantly present in its hyper-phosphorylated form (FIG. 5). The data presented in FIG. 5 demonstrating AAV2 mediated Rb hyper-phosphorlation correlates with our FACS analysis which indicated that many of the AAV infected cells had died with an S phase DNA content (FIG. 1).

Significance of Observed Results

AAV2 is a ubiquitous, non-pathogenic virus and as such is part of the normal flora of the human anogenital region. Thus, selective positioning of AAV in the same tissue infected by HPV places AAV2 in a unique position to inhibit HPV infections and viral DNA replication. Our results suggest that AAV2 selectively mediates apoptosis as a mode of oncosuppression in the HPV31b positive cell line, but not in primary human foreskin keratinocyte lines. These results are consistent with the idea that an ideal cancer therapeutic agent would specifically target tumor cells while leaving the surrounding healthy cells intact. Our results suggest that such a ideal situation could be achieved utilizing the wild-type AAV2 infectious particles and suggest a unique method for the gene therapy of cervical cancer.

Example 2

We had previously demonstrated that infection with the nonpathogenic adeno-associated virus type 2 (AAV2) induced cell death by apoptosis of cervical cancer cells approximately 6 days post-AAV2 infection. When normal, noncancerous cells are infected by AAV2 the cells do not undergo cell death by apoptosis displaying no cytopathic effects. We have now expanded these findings in the following ways.

1) We now have data to show that AAV2 can induce cell death of cervical cancer cells at all stages of carcinogenic progression: preneoplastic cervical intraepithelial neoplasia I (CIN-1) up to cervical invasive carcinoma cells.

| CELL LINE | CANCER STAGE REPRESENTED | CELL DEATH |
|---|---|---|
| CIN-612 9E | CIN-I (HPV316) | +++ |
| CIN-612 6E | CIN-II (HPV316) | +++ |
| W12 | CIN-I/II (HPV16) | +++ |
| HPV16 | CIN-I (HPV16) | +++ |
| RECA | INVASIVE CARCINOMA (HPV16) | +++ |
| HPV18 | CIN-I (HPV18) | +++ |
| AWCA | INVASIVE CARCINOMA(HPV18) | +++ |
| C33A | INVASIVE CARCINOMA (no HPV) | +++ |
| HFK | NORMAL KERATINOCYTE | NO |

+++ = 100% cell death
++ = 50-75% cell death
+ = 25-50% cell death

2) We now have data to show that keratinocytes that are immortalized, representing the initial stages of carcinogenic progression, die following infection with AAV2 with kinetics similar to cervical cancer cells.

| CELL LINE | CANCER STAGE REPRESENTED | CELL DEATH |
|---|---|---|
| N-TERTS | IMMORTALIZED | + |
| NIKS | IMMORTALIZED | +++ |
| HaCats | IMMORTALIZED | +++ |

3) We now have data to show that cancers besides cervical cancer can be induced to die following infection by AAV2.

| CELL LINE | CANCER TYPE | CELL DEATH |
|---|---|---|
| SCC | Squamous cell carcinoma | +++ |
| MCF-7 | Breast carcinoma | +++ |
| PC-3 | Prostate carcinoma | ++ |
| UACC-903 | Melanoma | + |

We now have reproducible results showing 100% killing.

When these experiments were initiated our primary goals were to investigate the effects of AAV2 on cell cycle regulatory proteins in HPV-infected cervical cancer cells. Studies reported elsewhere have shown that AAV2 mediates a G1 specific cell cycle block in primary fibroblasts. When cell death was observed by apoptosis, a large number entered S-phase and could be correlated with AAV2 Rep protein expression. In addition, multiple studies have demonstrated that the AAV2 encoded Rep78 protein inhibits transcription from both viral and cellular promoters. Neither of these studies showed any data that would imply that AAV2 was causing any effects associated with cell death. We initially studied the effects of AAV2 infection of cervical cancer cells up to 24 hours post-AAV2 infection. We then thought it would be interesting to observe time points beyond the initial 24 hours endpoint. Some plates were allowed to grow for 6-7 days post-AAV2 infection. During this process cells were passaged twice when cells reached 80% confluency. We observed that all the cells on the plate that had been infected with AAV2 had died. Our initial thought was that this was just a chance happening and that something was just wrong with that plate of cells. We had not expected cell death to occur and had no reason to think that it would happen. Using the CIN-612 9E cell line we have now repeated this observation a total of 15 times with the same result, with repeated passaging, at 6-7 days post-AAV2 infection the cervical cells all undergo cell death. Further analysis has shown that cell death was by an apoptotic pathway, as determined by DNA laddering studies. In addition, AAV2 rep proteins were concurrently expressed which can be correlated with cell death.

Example 3

Figure 6:
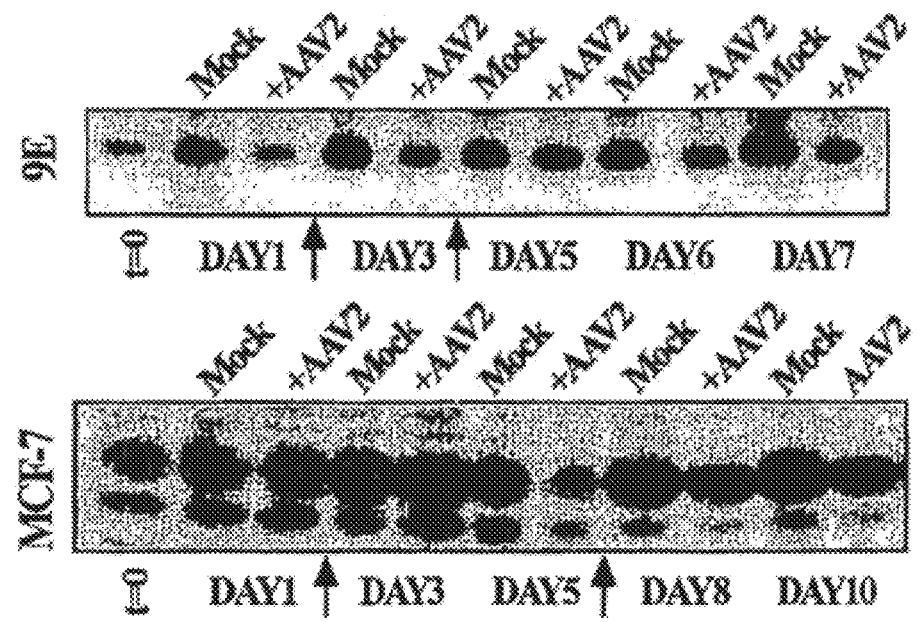
FIG. 6 shows the Western Blot analysis of Monolayer 9E and MCF-7 cells were infected with AAV2 at t=0. Cells were collected over a 7 day period, total proteins extracted, followed by western blot analysis using a polyclonal antibody against p21$^{WAF1}$. Arrows indicate times when cells were passaged upon confluency.

We previously observed that p21$^{WAF1}$ protein levels were downregulated in response to AAV2 infection in CIN-612 9E cells which maintain episomal copies of HPV31b. This result is interesting in light of the fact that the p21$^{WAF1}$ protein plays a central role in the induction of apoptosis. Lowering of p21$^{WAF1}$ protein level is a priming step for the apoptosis cascade. We now present results to shown that p21$^{WAF1}$ levels are also decreased in AAV2 infected MCF-7 breast cancer cells. FIG. 6 depicts this observation. Our results indicate that AAV2 mediated apoptosis in these two cancer lines may target similar pathways. The results are shown in FIG. 6. Monolayer 9E and MCF-7 cells were infected with AAV2 at t=0. Cells were collected over a 7 day period, total proteins extracted, followed by western blot analysis using a polyclonal antibody against p21$^{WAF1}$. Arrows indicate times when cells were passaged upon confluency.

Figure 7:
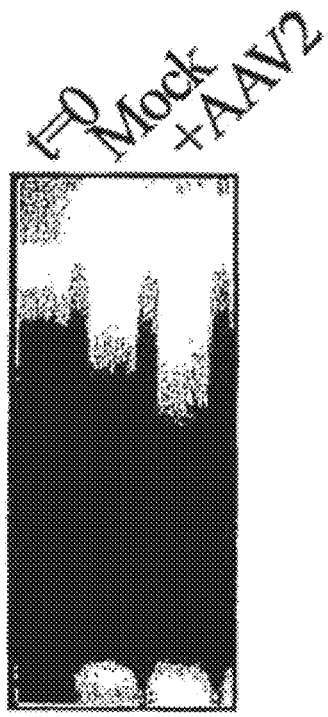
FIG. 7 is an autoradiogram showing the results of extraction of low molecular weight DNA and gel electrophoresis. DNA laddering was evident in AAV2 infected samples.

We have also previously observed that AAV2 infected CIN-612 9E cells undergo apoptotic cell death as evidenced by DNA laddering. We also detected DNA laddering in AAV2 infected MCF-7 cells. The results are shown in FIG. 7. Mock and AAV2 infected MCF-7 cells were harvested followed by extraction of low molecular weight DNA and agarose gel electrophoresis. DNA laddering was evident in AAV2 infected samples.

Figure 8:
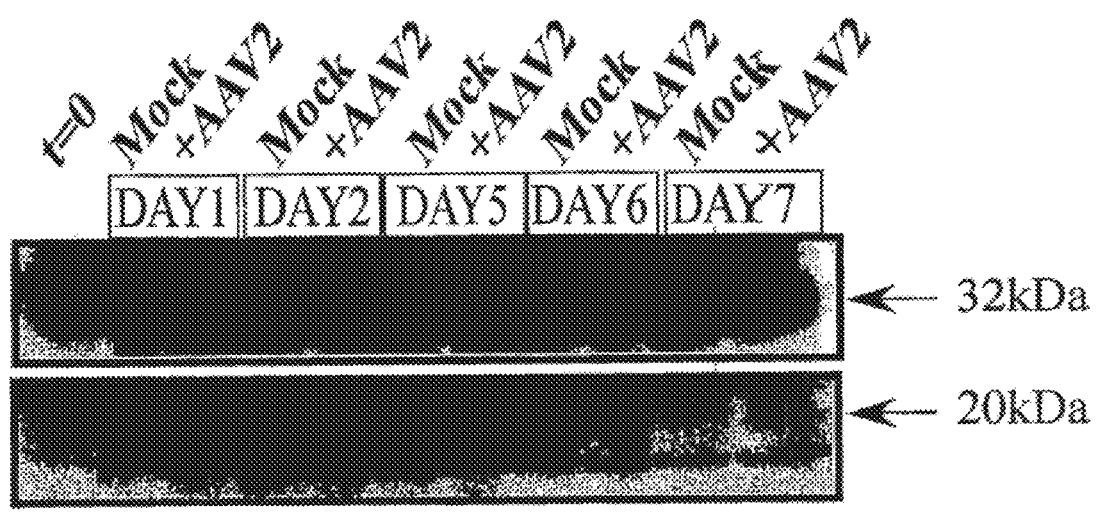
FIG. 8 shows the results of Western Blot analysis of a polyclonal antibody against Caspase-3 on monolayer CIN-612 9E cells infected with AAV2 at t=0. Cells were collected over a 7 day period, total proteins extracted, followed by western blot analysis. The 32 kDa holoenzyme was cleaved to its active form as depicted by the 20 kDa proteolytic fragment.

We further wanted to correlate apoptotic DNA laddering with activity of proteins involved in the execution of apoptosis. Since Caspase-3 is one of the last proteins to be activated in this cascade we performed western blots to look for evidence of Caspase-3 activation. We found that Caspase-3 was cleaved to its active form in AAV2 infected CIN-612 9E cells. The results are depicted in FIG. 8: Monolayer CIN-612 9E cells were infected with AAV2 at t=0. Cells were collected over a 7 day period, total proteins extracted, followed by western blot analysis using a polyclonal antibody against Caspase-3. The 32 kDa holoenzyme was cleaved to its active form as depicted by the 20 kDa proteolytic fragment.

Cumulatively, so far our data indicates that AAV2 mediated regulation of cell cycle proteins couple with downstream pathways which control apoptosis.

What is claimed is:

1. A method of killing squamous cell carcinoma breast cancer, prostate cancer, or melanoma cells comprising:
   administering to said sells an effective amount of a naturally occurring, non-modified AAV2 virus so that said virus will selectively induce apoptosis in said cancer cells in the absence of any anti-cancer compound or chemotherapeutic agent.

2. A method of treating squamous cell carcinoma, breast cancer, prostate cancer, or melanoma comprising:
   administering to a patient in need of such treatment, an effective amount of a pharmaceutical composition comprising a naturally occurring, non-modified AAV2 virus and a pharmaceutically acceptable carrier or excipient.

3. The method of claim 2 wherein said effective amount is from about 1.0 pfu/kg body weight to about $10^{15}$ pfu/kg body weight.

4. The method of claim 2 wherein said administration is by injection, intravenously, intravascularly, intramuscularly, subcutaneously, intraperitoneally, topically, orally, nasally, or by inhalation.

5. The method of claim 2 wherein said administration is as a single dose or in multiple doses.

6. The method of claim 2 wherein said method of further comprises a surgery to remove said cancer cell or a radiation therapy.

* * * * *

UNITED STATES PATENT AND TRADEMARK OFFICE
CERTIFICATE OF CORRECTION

| | | |
|---|---|---|
| PATENT NO. | : 8,080,240 B2 | Page 1 of 1 |
| APPLICATION NO. | : 11/577782 | |
| DATED | : December 20, 2011 | |
| INVENTOR(S) | : Meyers et al. | |

It is certified that error appears in the above-identified patent and that said Letters Patent is hereby corrected as shown below:

<u>Col. 1, lines 15-18:</u>
After GRANT REFERENCE, DELETE: "Work for this invention was funded in part by a grant from the United States Department Government National Institutes of Health, NIH Grant Number CA79006. The Government may have certain rights in this invention."

After GRANT REFERENCE ADD: --This invention was made with government support under Grant No. CA079006, awarded by the National Institutes of Health. The Government has certain rights in the invention.--

Signed and Sealed this
Twenty-eighth Day of August, 2012

David J. Kappos
*Director of the United States Patent and Trademark Office*